United States Patent [19]

Windorski et al.

[11] Patent Number: 4,509,506

[45] Date of Patent: Apr. 9, 1985

[54] SHIELDING DEVICE FOR RADIOACTIVE SEED

[75] Inventors: David C. Windorski, Cottage Grove; David O. Kubiatowicz, White Bear Lake, both of Minn.

[73] Assignee: Minnesota Mining & Manufacturing Co., St. Paul, Minn.

[21] Appl. No.: 262,760

[22] Filed: May 11, 1981

[51] Int. Cl.³ .............................................. A61J 1/00
[52] U.S. Cl. ................................. 128;1.2; 250/506.1
[58] Field of Search .................................. 128/1.1, 1.2; 250/506.1, 515.1, 517.1

[56] References Cited

U.S. PATENT DOCUMENTS

| | | | |
|---|---|---|---|
| 2,153,889 | 4/1939 | Hames | 128/1.1 |
| 2,862,108 | 11/1958 | Meilink | 128/1.2 |
| 3,669,093 | 6/1972 | Sauerwein et al. | 128/1.1 |

OTHER PUBLICATIONS

Martinez et al., "International Journal of Radiation Oncology & Biological Physics", vol. 5, No. 3, Apr. 1979, pp. 411–413.

*Primary Examiner*—William E. Kamm
*Attorney, Agent, or Firm*—Donald M. Sell; James A. Smith; Carolyn A. Bates

[57] ABSTRACT

Radioactive seeds contained in a suture material are shielded during shipping and storage inside a curved tube of dense material having two open ends. The suture material protrudes through at least one end of the tube. Preferably, one end of the suture material has removable means for preventing the end from entering the tube prematurely, and the other end is attached to a needle.

The seeds spaced from the open ends of the curved tube so as to prevent radiation from escaping from the tube.

6 Claims, 2 Drawing Figures

4,509,506

SHIELDING DEVICE FOR RADIOACTIVE SEED

FIELD OF THE INVENTION

This invention relates to the field of radiation therapy. More specifically, it relates to radioactive "seeds" which are implanted into diseased tissue to provide sustained radiation therapy. In particular, the invention relates to a novel shielding device for minimizing radiation exposure to individuals handling the seeds prior to and during implantation.

BACKGROUND ART

Implantable radioactive seeds for use in radiation therapy are described in U.S. Pat. No. 3,351,049. The seeds described therein comprise a tiny sealed capsule having an elongate cavity containing the radioisotope adsorbed onto a carrier body. The seeds are implanted directly into the diseased tissue. Because radioisotopes having short half-lives and emitting low energy X-rays, such as iodine-125, are used, the seeds can be left in the tissue indefinitely without excessive damage to surrounding healthy tissue or excessive radiation exposure to individuals in the patient's environment.

The use of absorbable sutures as carriers for iodine-125 seeds has greatly improved the ease and precision with which the seeds can be implanted into the tissue. Typically, each suture is loaded with up to twenty seeds, spaced one centimeter apart, and provided with a needle at one end. The object is to fill the body of the tumor, or tissue from which the tumor was excised, with radioactive seeds, set one centimeter equidistant from one another, to provide homogeneous radiation throughout the implanted volume. This is conveniently done by threading lengths of suture, loaded with seeds, through the tissue to be irradiated. Basic techniques for implanting the seed-carrying sutures into malignant tissue are described in "Surgical Radiation Therapy with Vicryl-$^{125}$I Absorbable Sutures", W. P. Scott, et al, *Surgery, Gynecology and Obstetrics*, Vol. 142, pp. 667–670, May, 1976.

One major problem associated with the use of radioactive seeds, particularly seeds contained within absorbable suture filament, involves packaging the seeds in a manner which allows for sterilization, yet minimizes radiation exposure to those individuals handling the seeds prior to and during implantation.

The most common method for shielding radioactivity is through the use of lead containers. Iodine-125 seeds are presently available commercially in lead storage/shipping containers (Medical Products Division of 3M, St. Paul, MN). The seeds are placed in glass vials inside the lead container. Before implantation into the tissue, the glass vials are removed from the lead container, the caps loosened, and the vials sterilized by steam or ethylene oxide. The seeds are then generally placed in a sterile shielding container of, for example, stainless steel, and transported to the operating room. Thus, for brief periods of time before and after sterilization and during the implantation procedure, the seeds are unshielded and those handling them are exposed to some radiation hazard.

Iodine-125 seeds in an absorbable suture carrier are not presently available commercially. However, methods for inserting the seeds into suture are known. (See for example, "A Method for Inserting I-125 Seeds into Absorbable Sutures for Permanent Implantation in Tissue", Bernice B. Palos et al., *Int. J. Radiation Oncology Biol. Phys.*, Vol. 6, pp. 381–385, March, 1980. Radioactive seeds in this form pose an even greater risk of radiation exposure during implantation than individual seeds, because the seeds are physically attached to each other and must be handled in groups instead of individually.

SUMMARY OF THE INVENTION

The present invention effectively eliminates the aforementioned problem of radiation exposure to those handling radioactive seeds during implantation. Furthermore, the invention allows a plurality of radioactive seeds in a string-like carrier to be shipped, stored, sterilized, and delivered to the tissue in a single shielding device.

According to the present invention there is provided a device for handling radioactive seeds comprising a curved tube of dense material open at both ends, having an interior diameter large enough to allow the seeds to be moved freely therein and side walls of sufficient thickness to prevent radiation from penetrating therethrough. Contained within the tube is a plurality of radioactive seeds arranged consecutively and spaced apart in a string-like carrier. Preferably, one end of the string-like carrier extends through one of the open ends of the tube and contains removable means to prevent the end of the carrier from entering the tube and the seeds escaping prematurely from the opposite end of the tube. The opposite end of the carrier extends through the other open end of the tube and, preferably, is attached to needle means for penetrating body tissue. The seeds are disposed within the curved portion of the tube and spaced far enough from either open end of the tube to prevent radiation from escaping from the ends of the tube.

The curved, preferably circular, shape of the tube allows the ends of the tube to be left open to facilitate sterilization of the contents without permitting primary and scattered radiation from escaping through the open ends. This is possible because radioactive emissions travel in a straight path and cannot bend around corners and curves. Because of the placement of the seeds within the tube, radioactive emissions strike the curved wall of the tube and cannot escape from the open ends.

The seeds can be sterilized in the shielding tube and sealed in a sterile package for shipment and storage. The seeds are ready for implantation without further handling. Just prior to implantation, the removable means, e.g., a paper tab, for preventing one end of the string-like carrier from entering the tube is removed, and the carrier is pulled from the other end of the tube into the tissue along the path determined by the surgeon. Maximum shielding of operating room personnel from radiation is accomplished since the seeds remain in the shielding tube up to the very time of implantation.

DESCRIPTION OF THE DRAWINGS

The invention may be further understood by reference to the accompanying drawings wherein like numerals refer to like elements and.

Figure 1:
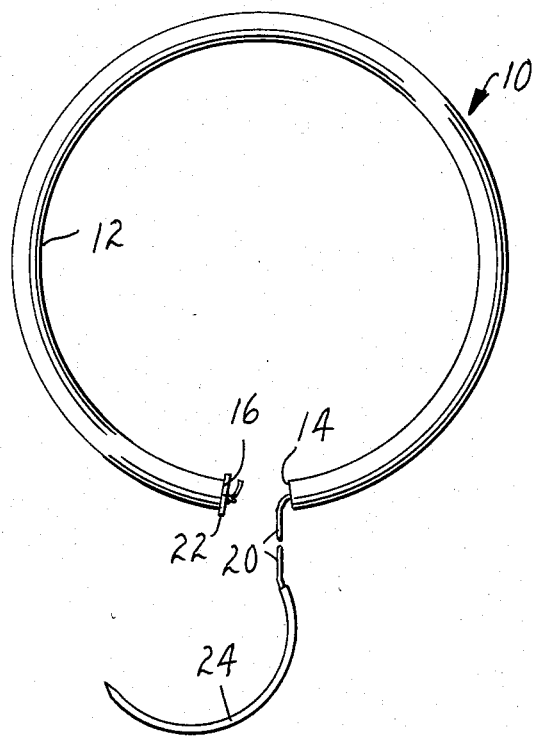
FIG. 1 is a top plan view of the handling device of the invention.
Figure 2:
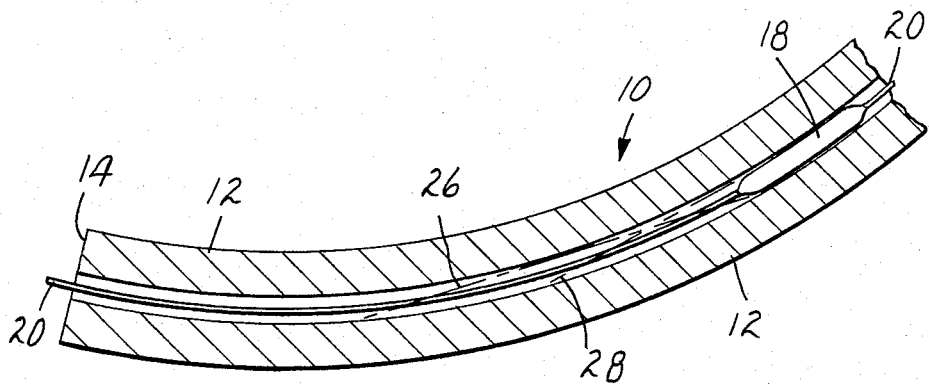
FIG. 2 is an enlarged transverse sectional view of one end of the device.

Referring now to the drawings, the device 10 comprises a curved tube having two open ends 14 and 16. The tube is preferably circular as illustrated with the two open ends opposing one another. The tube may be formed of any dense material which will prevent penetration of radiation from the radioactive seeds inside the tube. Stainless steel is the material of choice because it is easily formable, readily available, resistant to corrosion and of low toxicity. Lead, lead-filled plastic and other dense materials such as tungsten, silver, copper, nickel and iron can be used, but are less preferred. Contained within tube 12 is a plurality of radioactive seeds 18 (only one is illustrated in FIG. 2) which are arranged consecutively and spaced apart on a string-like carrier 20. The radioactive seeds useful in the practice of the invention are preferably those described in U.S. Pat. No. 3,351,049. The seeds contain radioactive isotopes which emit radiation principally limited to low energy X-rays and which have half-lives sufficiently short that they decay predictably, i.e., with a known radioactive half-life, to a negligible output level and therefore can be left permanently implanted in the tissue. Iodine-125 is the preferred radioactive isotope for use in the seeds. Iodine-125 seeds are available commercially from the Medical Products Division of 3M, St. Paul, Minn.

String-like carrier 20 is preferably an absorbable suture such as Vicryl ® (Polyglactin 910) manufactured by Ethicon Inc., Summerville, N.J. A method for inserting the seeds into the suture is described in *Int. J. Radiation Oncology Biol. Phys.*, Vol. 6, supra. Basically, the method involves the following steps:

(1) The waxed end of the suture is cut off.

(2) The inner core is exposed and the sheath pressed back from the inner core as far as possible.

(3) The core is cut and the sheath allowed to spring back to its full length.

(4) A stylet is placed in a vise so that it is held horizontally facing away from the operator.

(5) The hollow sheath is slipped over the stylet and bunched together to expand the sheath to its maximum diameter.

(6) The sheath is pushed back off the stylet. (It should not be pulled off as this causes the sheath to tighten up and cling to the stylet.)

(7) Using forceps, the first seed is inserted into the sheath and worked one centimeter down.

(8) The sheath is slipped onto the stylet using rubber tipped forceps until the stylet is in contact with the seed.

(9) Using rubber tip forceps, the sheath is gripped close to the tip of the stylet. The sheath is then drawn one-half centimeter down onto the stylet. This pushes the seed one-half centimeter into the sheath. This is repeated at one-half centimeter per draw until the seed is at the desired depth into the sheath.

(10) The sheath is pulled off the stylet and steps 7–9 are repeated for the rest of the seeds.

Typically 2 to 20 seeds are loaded in a single suture for insertion into tube 12. The end of carrier 20 protruding through end 16 of tube 12 is fitted with a cardboard tab 22 or other removable means for preventing the end of carrier 20 from entering the open end of the tube. The other end of carrier 20 protruding through open end 14 of the tube 12 is preferably attached to a needle 24. Needle 24 is used to draw carrier 20 into the tissue and deposit seeds 18 at the desired locations. The seeds in the carrier 20 may be inspected by pulling the carrier from tube 12 at one end by means of tab 22. Carrier 20 may be removed through open end 14 of tube 12 by first removing tab 22.

An excess length of suture is generally provided between needle 24 (when present) and open end 14 of tube 12. For convenient packaging, the tube is preferably mounted on a support (not shown) such as a stiff paper card having slots therein to secure the tube to the support. Additional anchoring means are provided on the support around which the excess suture may be wound.

The preferred embodiment of tube 12 is made of type 304 stainless steel tubing having an outside diameter of 0.188 inch and an inside diameter of 0.058 inch. These tubing dimensions provide 99.99 percent shielding for photons and X-rays emitted from iodine-125. The preferred tube is 24 centimeters long and is bent into a circular shape having a diameter of 8.5 centimeters. As illustrated in FIG. 2, the terminal seed 18 on carrier 20 is located far enough from the open end of the tube that straight line radiation emissions from the seed (shown as dotted lines 26 and 28) strike the interior walls of tube 12 and do not escape nor are scattered through the ends of the tube.

Tube 12 containing the seeds in the suture carrier is positioned near the implant site. When the needle end of the carrier is sewn into the tissue, tab 22 is removed. The needle end is then pulled and the seeds exit the tube and are positioned in the tissue. The extra length of suture is cut off.

The device of the invention effectively minimizes radiation exposure to handlers of the seeds before and during the implantation procedure.

What is claimed is:

1. A device for handling radioactive seeds comprising:
   a. a curved tube of dense material open at both ends, said tube having an interior diameter larger than said seeds to allow said seeds to be moved freely therein and side walls of sufficient thickness to prevent radiation from penetrating therethrough;
   b. a length of suture material located within said tube and not protruding through at least one of said open ends;
   c. removable stop means attached to at least end of said suture material for preventing said end of said suture material from entering said tube; and
   d. a plurality of surgically-implantable radioactive seeds within said tube arranged consecutively and spaced apart in said suture material, said seeds being spaced from said open ends so as to prevent radiation from escaping from said open ends.

2. A device for handling radioactive seeds comprising:
   a. a curved tube of dense material open at both ends, said tube having an interior diameter larger than said seeds to allow said seeds to be moved freely therein and side walls of sufficient thickness to prevent radiation from penetrating therethrough;
   b. a length of suture material located within said tube having a first end protruding through one of said open ends of said tube and a second end protruding through the other of said open ends;
   c. removable means attached to said first end of said suture material for preventing said first end from entering said tube;
   d. needle means attached to said second end of said suture material for penetrating body tissue; and
   e. a plurality of surgically-implantable radioactive seeds within said tube arranged consecutively and spaced apart in said suture material, said seeds being spaced from said open ends so as to prevent radiation from escaping from said open ends.

3. The device according to claim 2, wherein said tube is stainless steel.

4. The device according to claim 2, where said tube is circular in shape with said open ends opposing one another.

5. The device according to claim 2, wherein said seeds contain iodine-125.

6. The device according to claim 2, wherein said suture material is absorbable.

* * * * *